United States Patent [19]

Arcamone et al.

[11] Patent Number: 4,738,980
[45] Date of Patent: Apr. 19, 1988

[54] DISTAMYCIN DERIVATIVES AND PROCESS FOR THEIR PREPARATION

[75] Inventors: Federico Arcamone; Nicola Mongelli; Fabio Animati, all of Milan, Italy

[73] Assignee: Farmitalia Carlo Erba, S.p.A., Milan, Italy

[21] Appl. No.: 783,508

[22] Filed: Oct. 3, 1985

[30] Foreign Application Priority Data

Jul. 16, 1985 [GB] United Kingdom ............... 8517923

[51] Int. Cl.$^4$ .................... A61K 31/40; C07D 403/14
[52] U.S. Cl. .................................... 514/422; 548/518
[58] Field of Search ................... 548/518; 514/422

[56] References Cited

U.S. PATENT DOCUMENTS

| 3,420,844 | 1/1969 | Arcamore et al. ............. 548/518 |
| 3,420,845 | 1/1969 | Arcamore et al. ............. 548/518 |
| 3,432,522 | 3/1969 | Preau ............................ 548/518 |

FOREIGN PATENT DOCUMENTS

| 547128 | 10/1957 | Canada ........................ 548/518 |
| 557568 | 5/1958 | Canada ........................ 548/518 |
| 1421245 | 11/1965 | France. |
| 1004974 | 3/1964 | United Kingdom. |
| 1009797 | 8/1964 | United Kingdom. |
| 1061639 | 7/1965 | United Kingdom. |

OTHER PUBLICATIONS

Nikitin, S. M., "DNA Base Pair Sequence-Specific Ligands . . .", Chemical Abstracts, vol. 95, 1981, p. 32; 95:35304r.
Grehn, L. "Synthesis and Antiviral Activity of Distamycin A Analogues . . .", J. Med. Chem., 1983, 26, 1042-1049.
Taylor, J. S. et al, "DNA Affinity Cleaving" Tetrahedron 40,3,457 (1984).
Schultz, P. G. et al, "Sequence Specific Double Strand Cleavage of DNA by Bis(EDTA-DistamycinFC$^{II}$) and EDTA-Bis(Distamycin)Fe$^{II}$" Am. Chem. Soc. 105,26,7748 (1983).
Arcamone, F. "On Distamycin and Related Compounds, Selective Antiviral Agents" Med. Chem. 1972, pp. 29-45.
Bialer, M. et al, "Structure-Activity Relationship . . ." Jour. of Med. Chem., 1979, vol. 22, No. 11, pp. 1296-1301.
Chandra, P. et al, "Some Structural Requirements for the Antibiotic Action of Distamycin" FEBS Letters, vol. 16, No. 4, Sep. 1971 pp. 249-252.
Kuroyedov, A. A. et al, "Distamycin A and its Analogs as Agents for Blocking of Endo R. EcoRI Activity" Gene, 1(1977) 389-395.
Arcamone, F. et al, "Structure and Synthesis of Distamycin A" Nature, Sep. 5, 1964, vol. 203, pp. 1064-1065.
Luck, G. et al, "Specific Interactions of Distamycin A . . ." Nucleic Acids Research, vol. 4, No. 8, Aug. 1977, pp. 2655-2671.
Kopka, M. L. et al, "The Molecular Origin of DNA--Drug Specificity . . ." Proc. Natl. Acad. Sci. USA vol. 82, pp. 1376-1380, Mar. 1985, Biochemistry.

(List continued on next page.)

Primary Examiner—Donald G. Daus
Assistant Examiner—William A. Teoli, Jr.
Attorney, Agent, or Firm—Murray and Whisenhunt

[57] ABSTRACT

Distamycin A derivatives of formula

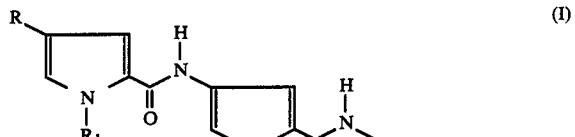

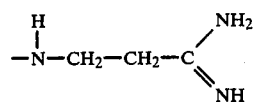

wherein
R is (a)—NHR$_3$, wherein R$_3$ is
 (a')—CON(NO)R$_4$, in which R$_4$ is C$_1$-C$_4$ alkyl either unsubstituted or substituted by halogen; or
 (b')—CO(CH$_2$)$_m$—R$_5$, in which R$_5$ is halogen, oxiranyl, methyloxiranyl, aziridinyl, a group

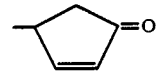

or a group

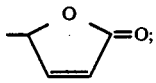

and m is zero or an integer of 1 to 4; or
(b)

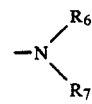

wherein either R$_6$ and R$_7$ are the same and are each oxiranemethyl, aziridinemethyl, or C$_2$-C$_4$ alkyl 2-substituted by halogen or by a group —OSO$_2$R$_8$, wherein R$_8$ is C$_1$-C$_4$ alkyl or phenyl, or one of R$_6$ and R$_7$ is hydrogen and the other is as defined above; and each group R$_1$ is, independently, hydrogen or C$_1$-C$_4$ alkyl, and the pharmaceutically acceptable salts thereof.

The compounds are useful as antiviral or antitumor agents.

6 Claims, No Drawings

OTHER PUBLICATIONS

Youngquist, R. S. et al, "Sequence-Specific Recognition . . . Proc. Natl. Acad. Sci. USA vol. 82, pp. 2565–2569 May 1985, Biochemistry.
Chemical Abstracts: 68:21767z, 68:21768a, 88:83397a, 88:201h, 97:215877e, 82:25984e, 99:176269c, 95:61898g, 89:102109x, 81:163162r, 100:39669h.
Chem. Abstracts: 84:150434t, 90:87174q, 88:50585g.
Chemical Abstracts: 68:87088k, 71:101629h, 71:101631c.
Chem. Abstracts: 79:38445t.
Chem. Abstracts: 77:14824y, 76:108639y, 76:149456e.
Penco, S. et al, "Distamicina A–Nota II . . . " Gazz. Chim. Ital., 97(1967) pp. 1110–1115.
Martinez, J. "Activated N–Nitrosocarbomates for . . . " J. Med. Chem. 1982, 25 pp. 178–182.
Chandra, et al. "Some Structrual Requirements for the Antibiotic . . . " Feb. Letters, Jan. 1972, vol. 19 #4, pp. 327–330.
Waehnert, U. et al, "Dependent Inactivation of the DNA . . . " Chemical Abstracts, vol. 83, 1975 p. 252.
Zimmer, C. et al, "Binding of Analogs of the Antibiotics . . . " Chemical Abstracts, vol. 76, 1972, p. 180.
Nikitin, S. M. et al, "DNA Base Pair Sequence Specific Ligands . . . " Institute of Molecular Biology, Academy of Science of the USSR, Moscow, pp. 542–551.

DISTAMYCIN DERIVATIVES AND PROCESS FOR THEIR PREPARATION

The invention relates to distamycin derivatives, to a process for their preparation and to pharmaceutical compositions containing them.

Distamycin A is a well known compound having the following formula

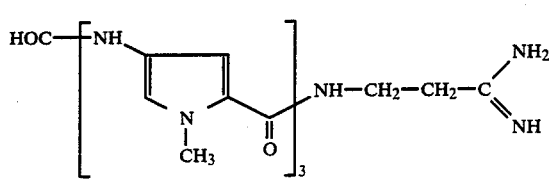

Literature referring to distamycin A includes, for example, Nature 203, 1064 (1964).

The invention provides distamycin A derivatives having the following general formula (I)

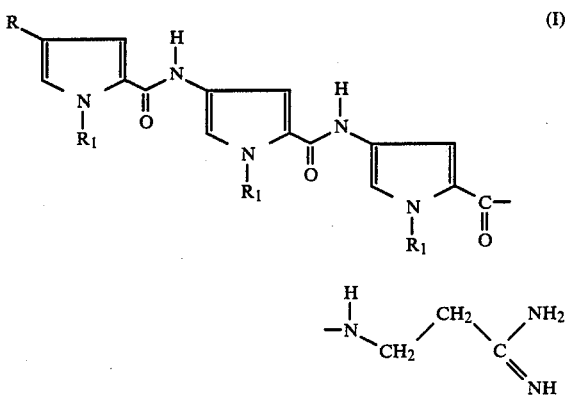

wherein
R is (a) —NHR$_3$, wherein R$_3$ is
  (a′) —CON(NO)R$_4$, in which R$_4$ is C$_1$–C$_4$ alkyl either unsubstituted or substituted by halogen; or
  (b′) —CO(CH$_2$)$_m$—R$_5$, in which R$_5$ is halogen, oxiranyl, methyloxiranyl, aziridinyl, cyclopropyl or an alicyclic α,β-unsaturated ketone or lactone, and m is zero or an integer of 1 to 4; or
(b)

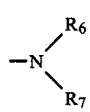

wherein either R$_6$ and R$_7$ are the same and are each oxiranemethyl, aziridinemethyl, or C$_2$–C$_4$ alkyl 2-substituted by halogen or by a group —OSO$_2$R$_8$, wherein R$_8$ is C$_1$–C$_4$ alkyl or phenyl, or one of R$_6$ and R$_7$ is hydrogen and the other is as defined above; and
each group R$_1$ is, independently, hydrogen or C$_1$–C$_4$ alkyl.

The invention includes also the pharmaceutically acceptable salts of the compounds of formula (I) as well as all the possible isomers covered by the formula (I), both separately and in mixture.

When R$_4$ is unsubstituted C$_1$–C$_4$ alkyl, methyl and ethyl are preferred, in particular methyl.

When R$_4$ is C$_1$–C$_4$ alkyl substituted by halogen, the halogen is, preferably, chlorine or bromine; in this case preferred R$_4$ values are chloroethyl and fluoroethyl.

When R$_5$ is halogen, it is, preferably, chlorine or bromine.

When R$_5$ is methyloxiranyl, it may be either 2-methyloxiranyl

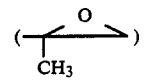

or 3-methyloxiranyl

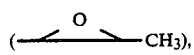

preferably being 3-methyloxiranyl.

When R$_5$ is halogen, it is, preferably, chlorine or bromine.

When R$_5$ is an alicyclic α,β-unsaturated ketone or lactone, it is, e.g., a group

or, respectively, a group

Preferred R$_5$ values are oxiranyl

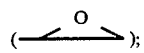

1-aziridinyl

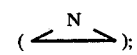

cyclopropyl

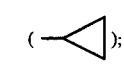

a group

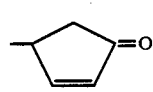

or a group

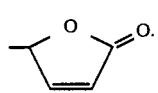

Preferred m values are zero, 1 or 2.

A R$_6$/R$_7$ C$_2$-C$_4$ alkyl group 2-substituted by halogen is, preferably, 2-chloroethyl.

A R$_6$/R$_7$ C$_2$-C$_4$ alkyl group 2-substituted by a group —OSO$_2$R$_8$ is, preferably, a group —CH$_2$—CH$_2$—OSO$_2$R$_8$, wherein R$_8$ is C$_1$-C$_4$ alkyl, preferably methyl.

Preferably each group R$_1$, independently, is C$_1$-C$_4$ alkyl, in particular methyl and, most preferably, all groups R$_1$ are methyl.

As already said, the invention includes also the pharmaceutically acceptable salts of the compounds of formula (I). The salts includes both the salts with pharmaceutically acceptable acids, either inorganic acids such as, e.g., hydrochloric, hydrobromic, nitric and sulfuric, or organic acids such as, e.g., citric, tartaric, maleic, fumaric, methanesulfonic and ethanesulfonic.

A preferred class of compounds under this invention is represented by the compounds of formula (I) wherein R is —NHR$_3$ wherein R$_3$ is (a') —CON(NO)R$_4$ wherein R$_4$ is C$_1$-C$_4$ alkyl substituted by halogen, or (b') —CO(CH$_2$)$_m$—R$_5$ wherein R$_5$ is halogen, oxiranyl, 1-aziridinyl, cyclopropyl, or an alicyclic α,β-unsaturated lactone, and m is zero, 1 or 2;

each group R$_1$ is, independently, C$_1$-C$_4$ alkyl, and the salts thereof with pharmaceutically acceptable acids, in particular with hydrochloric acid.

In the above preferred class a R$_4$ or R$_5$ C$_1$-C$_4$ alkyl group is, preferably, methyl or ethyl; a halogen atom is, preferably, chlorine; an alicyclic α,β-unsaturated lactone is, preferably, a group

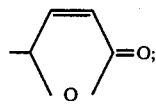

a R$_1$ C$_1$-C$_4$ alkyl group is, preferably, methyl.

A particularly preferred group of compounds in the ambit of the above preferred class are the compounds of formula (I) wherein R is —NHR$_3$ wherein R$_3$ is (a') a group —CON(NO)R$_4$ wherein R$_4$ is —CH$_2$—CH$_2$—Cl, or (b') a group —CO(CH$_2$)$_m$—R$_5$ wherein either m is 1 or 2 and R$_5$ is chlorine, or m is zero and R$_5$ is oxiranyl, 1-aziridinyl or cyclopropyl, or m is 2 and R$_5$ is

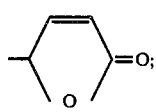

each group R$_1$ is methyl,
and the salts thereof with pharmaceutically acceptable acids, in particular hydrochloric acid.

Another preferred class of compounds under this invention are the compounds of formula (I) wherein
R is

wherein R$_6$ and R$_7$ are the same and are each oxiranemethyl, 1-aziridinemethyl, or a C$_2$-C$_4$ alkyl group 2-substituted by halogen or by a group —OSO$_2$R$_8$ wherein R$_8$ is C$_1$-C$_4$ alkyl; each group R$_1$ is, independently, C$_1$-C$_4$ alkyl;
and the salts thereof with pharmaceutically acceptable acids, in particular with hydrochloric acid.

In the above preferred class a C$_2$-C$_4$ alkyl group in R$_6$/R$_7$ is, preferably, ethyl; a halogen is, preferably, chlorine; when R$_6$ and R$_7$ are a C$_2$-C$_4$ alkyl group 2-substituted by halogen, they are, preferably, 2-chloroethyl; when R$_6$ and R$_7$ are a C$_2$-C$_4$ alkyl 2-substituted by a group —OSO$_2$R$_8$ where R$_8$ is C$_1$-C$_4$ alkyl, they are, preferably, methanesulfonyloxyethyl; a C$_1$-C$_4$ alkyl group for R$_1$ is, preferably, methyl.

A particularly preferred group of compounds within the hereabove said preferred class are the compounds of formula (I) wherein
R is

wherein R$_6$ and R$_7$ are both oxiranemethyl, 1-aziridinemethyl, 2-chloroethyl or methanesulfonyloxyethyl;

each group R$_1$ is methyl,
and the salts thereof with pharmaceutically acceptable acids, in particular with hydrochloric acid.

Specific examples of preferred compounds under this invention, especially in the form of salts with hydrochloric acid, are the following:

N-deformyl-N-[N'-(2-chloroethyl)-N'-nitrosocarbamoyl]-Distamycin A;

N-deformyl-N-[N'-methyl-N'-nitrosocarbamoyl]-Distamycin A;

N-deformyl-N-(oxiranecarbonyl)Distamycin A;

N-deformyl-N-(cyclopropylcarbonyl)Distamycin A;

N-deformyl-N-(3-methyloxiranecarbonyl)Distamycin A;

N-deformyl-N-(2-chloroethylcarbonyl)Distamycin A;

N-deformyl-N-[1-(aziridine)carbonyl]Distamycin A;

N-deformyl-N-[N,N-bis(2-chloroethyl)]Distamycin A.

The compounds object of the invention can be prepared by a process comprising:

(A) reacting a compound of formula (II)

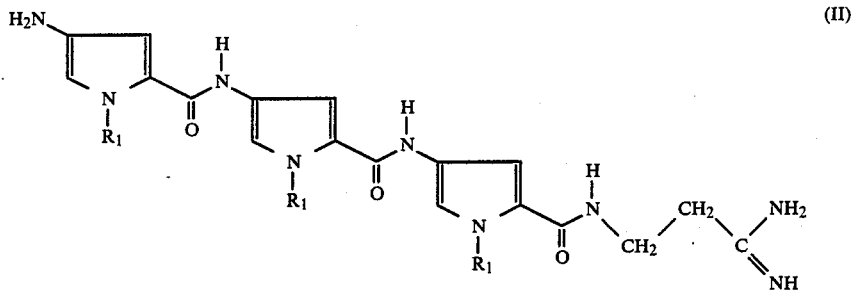

wherein
R₁ is as defined above, with a compound of formula (III)

wherein
R₄ is as defined above and Z is a leaving group, so obtaining a compound of formula (I) wherein R is —NHR₃ and R₃ is —CON(NO)R₄, wherein R₄ is as defined above; or (B) reacting a compound of formula (II), wherein R₁ is as defined above, with a compound of formula (IV)

$$Z'-CO-(CH_2)_m-R_5 \qquad (IV)$$

wherein
R₅ and m are as defined above and Z' is a leaving group, so obtaining a compound of formula (I) wherein R is —NHR₃ and R₃ is —CO(CH₂)$_m$—R₅, wherein m and R₅ are as defined above; or (C) reacting a compound of formula (II), wherein R₁ is as defined above, with a compound of formula (V)

wherein
X may be hydrogen, $C_1$-$C_2$ alkyl or halomethyl, to give a compound of formula (VI)

formula (VI) into a compound of formula (I) wherein R is

wherein R₆ and R₇ are as defined above; and, if desired, converting a compound of formula (I) into another compound of formula (I) and/or, if desired, salifying a compound of formula (I) or obtaining a free compound from a salt and/or, if desired, separating a mixture of isomers of formula (I) into the single isomers.

In the compounds of formula (III) the leaving group Z may be, e.g., an azido group or a trichlorophenoxy or succinimido-N-oxy group.

The reaction between a compound of formula (II) and a compound of formula (III) is preferably carried out in the presence of a solvent and, preferably, using an excess of the compound of formula (III), e.g. from about 1.1 to about 2 moles of compound (III) per 1 mole of compound (II). The solvent preferably is an inert organic solvent chosen e.g. from dialkylsulphoxides, e.g. dimethylsulphoxide, aliphatic acid dialkylamides, e.g. dimethylformamide or dimethylacetamide, phosphoric acid triamide or hexamethylphosphoramide, for example, dioxane or dimethoxyethane. Dimethylformamide (DMF) is a particularly preferred solvent. The reaction temperature may range from about −10° C. to about 25° C., although 0° C. is a particularly preferred temperature.

The time required for the reaction may vary within the range from about 0.5 to about 6 hours.

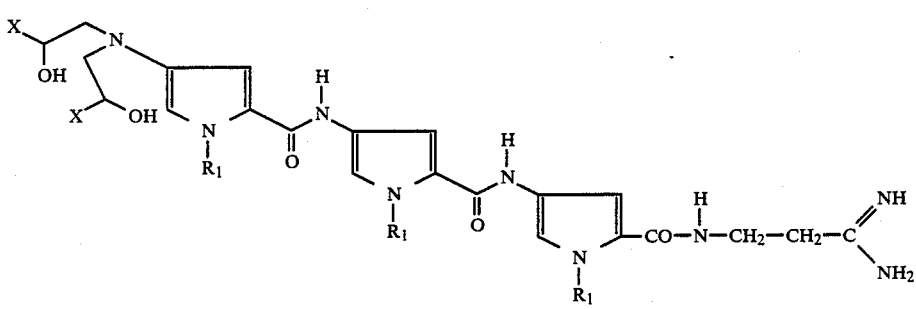

wherein
R₁ is as defined above and each X has the meaning corresponding to the meaning of X in the compound (V), and transforming a compound of The displaceable group Z' in the compound of formula (IV) may be, e.g., a halogen atom, e.g. chlorine or bromine, or an imidazolyl or phenoxy group.

The reaction between a compound of formula (II) and a compound of formula (IV) is preferably carried out in the presence of a solvent and, preferably, using an excess of the compound of formula (IV), e.g. from about 1.1 to about 2 moles of compound (IV) per 1 mole of compound (II). The solvent preferably is an inert organic solvent chosen from dialkylsulfoxides, e.g. dimethylsulfoxides, aliphatic acid dialkylamides, e.g., dimethylformamide, heterocyclic amines like pyridine, aliphatic alcohols and also water. A particularly preferred solvent is DMF.

The reaction temperature may range from about $-50°$ C. to about 50° C. The time required for the reaction may vary approximately within the range from 0.5 to 24 hours. When in the compound of formula (V) X is halomethyl, it is preferably, chloromethyl or bromomethyl.

The reaction between a compound of formula (II) and a compound of formula (V) is preferably carried out in the presence of a solvent and, preferably, using an excess of the compound of formula (V), e.g. from about 25 moles to about 50 moles of compound (V) per 1 mole of compound (II).

The solvent can be, e.g., water, an aliphatic alcohol, e.g. methanol or ethanol, an aliphatic carboxylic acid such as, e.g., acetic acid, an aliphatic acid dialkylamide, e.g. dimethylformamide, or a dialkylsulphoxide, e.g. dimethylsulphoxide, dioxane or dimethoxyethane. Methanol is a particularly preferred solvent.

The reaction temperature may range form about $-20°$ C. to about 25° C.

The time required for the reaction may vary within the range from about 2 to about 48 hours.

The transformation of a compound of formula (VI) into a compound of formula (I) wherein R is a group

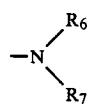

wherein $R_6$ and $R_7$ are as previously defined, may be carried out through reactions commonly used in the organic chemistry.

Thus, for example, a compound of formula (VI) wherein each group X is hydrogen or $C_1$-$C_2$ alkyl may be reacted with an halogenating agent such as, e.g., an halide, e.g. chlorine or bromine, or a thionyl halide, e.g. thionylchloride, to give a compound of formula (I) wherein R is a group

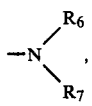

wherein each $R_6$ and $R_7$ is $C_2$-$C_4$ alkyl 2-substituted by halogen, e.g. chlorine or bromine. Similarly, a compound of formula (VI) wherein X is hydrogen or $C_1$-$C_2$ alkyl may be reacted with a sulfonic acid of formula $R_8SO_3H$, wherein $R_8$ is as defined above or, most preferably, with a reactive derivative thereof such as, e.g., the corresponding sulfonyl halide, e.g. chloride, or anhydride, to give a compound of formula (I) wherein R is a group

wherein each $R_6$ and $R_7$ is $C_2$-$C_4$ alkyl 2-substituted by a group $-O-SO_2R_8$ wherein $R_8$ is as defined above.

On the other hand, a compound of formula (VI) wherein each group X is halomethyl, e.g. chloromethyl or bromomethyl may be reacted with a base to give a compound of formula (I) wherein R is a group

wherein each $R_6$ and $R_7$ is oxiranemethyl.

The base may be either an inorganic base such as, for instance, an alkali metal, e.g. sodium or potassium, hydroxide, or an alkaline-earth metal, e.g. calcium or magnesium, hydroxide, or an organic base such as, for instance, an aliphatic amine, e.g. trimethylamine, or a heterocyclic amine, e.g. pyridine, piperidine, morpholine or methylmorpholine.

Other compounds of formula (I) wherein R is a group

may be prepared from a compound of formula (VI) through reactions well known in the organic chemistry and following known procedures.

Also the optional conversion of a compound of formula (I) into another compound of formula (I), the salification of a compound of formula (I) and the preparation of a free compound from a salt may be carried out according to known methods.

Conventional procedures, such as, e.g., fractional crystallization and chromatography, may also be used for the optional separation of a mixture of isomers of formula (I) into the single isomers.

The compound of formula (II) can be prepared by following known procedures, for example procedures analogous to those described for preparing distamycin derivatives in Gazz. Chim. Ital. 97, 1110 (1967).

Compounds of formula (III) are known compounds and they can be prepared, for example, according to J. Med. Chem. (1982), 25, 178–182.

Compounds of formula (IV) and (V) are known compounds too or may be prepared by known methods from known compounds. In particular, for instance, compounds of formula (IV) are either commercial compounds or can be prepared through activation of the carboxy parent compounds in a conventional way.

Compounds of formula (V) are commercially available compounds.

The compounds of the invention can be used as antiviral and antineoplastic agents.

They show, e.g., a remarkable effectiveness in interfering with the reproductive activity of the pathogenic viruses and protect tissue cells from viral infections. For example they show activity against DNA viruses such as, for instance, Herpes, e.g. Herpes simplex and Herpes zoster, viruses, and Adenoviruses, and against retroviruses such as, for instance, Sarcoma viruses, e.g., Murine sarcoma virus, and Leukemia viruses, e.g. Friend leukemia virus. The compounds of the invention show also cytostatic properties towards tumor cells.

Owing to the above activity the compounds of the invention are able, e.g., to inhibit the growth of various tumors, for instance breast carcinoma and tumors induced by viruses, e.g. Moloney Sarcoma virus.

The compounds of the invention can be administered by the usual routes, for example parenterally, e.g. by intravenous injection or infusion, intramuscularly, subcutaneously, or also topically.

The dosage depends on the age, weight and conditions of the patient and on the administration route. For example, a suitable dosage for administration to adult humans may range from about 0.1 to about 100 mg pro dose 1–4 times a day.

As already said, the invention includes also pharmaceutical compositions containing a compound of formula (I) as the active substance, in association with one or more pharmaceutically acceptable excipients. The pharmaceutical compositions of the invention are usually prepared following conventional methods and are administered in a pharmaceutically suitable form. For instance, solutions for intravenous injection of infusion may contain as carrier, for example, sterile water or preferably they may be in the form of sterile aqueous isotonic saline solutions.

Suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride. In the forms for topical application, e.g. creams, lotions or pastes for use in dermatological treatment, the active ingredient may be mixed with conventional oleaginous or emulsifying excipients.

The following examples illustrate but do not limit the invention.

The abbreviations DMF and THF stand for N,N-dimethylformamide and, respectively, tetrahydrofurane.

EXAMPLE 1

To a stirred solution of deformyl distamycin A dihydrochloride (2 g) in methanol (100 ml), cooled to $-10°$ C., cold ethylene oxide (20 ml) was added.

The reaction flask was sealed and allowed to reach room temperature overnight.

The methanol and the excess of ethylene oxide were removed under reduced pressure.

The residue was chromatographed on silica gel, washed with hydrochloric acid, using chloroform 70/methanol 30 as eluant, to give 1.32 g of N-deformyl-N-[N,N-bis-(2-hydroxyethyl)]Distamycin A hydrochloride;

U.V. $\lambda$max (EtOH 95%)($\epsilon$): 244 (24,140); 306 (27,142) nm;

MS m/e (f.d.): 542 $M^+ + 1$, 524 $M^+ - NH_3$; 471

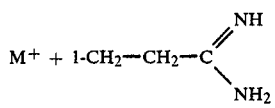

N.M.R. (DMSO-$d_6$) $\delta$: 2.63 (2H, t); 3.00–3.30 (4H, m); 3.3–3.7 (6H, m); 4.6 (2H, t); 6.25–7.25 (6H, m); 7.20 (1H, t); 7.62 (2H, s); 7.95 (2H, s); 9.62 (1H, s); 9.86 (1H, s).

EXAMPLE 2

A solution of N-deformyl-N,N-bis(2-hydroxyethyl)-distamycin A hydrochloride (680 mg) in pyridine (7 ml), cooled to 0°–5° C., was treated with methanesulfonylchloride (0.21 ml) in pyridine (2 ml) for 1 hour.

After addition of methanol (7 ml), the reaction mixture was warmed to room temperature.

The solvents were removed in vacuo and the residue was chromatographed on silica gel with chloroform-methanol 75:25 as eluant affording N-deformyl-N,N-bis(2-chloroethyl)-distamycin A hydrochloride (310 mg).

U.V. $\lambda$max (EtOH 95%) ($\epsilon$): 245 (21,139), 309 (21,273) nm.

MS m/e (f.d.): 578 $M^+ + 1$, 559 $M^+ - NH_4^+$, 505 $M^+ - CHCl$, 452 $M^+ + 1 - 2(CH_2CH_2Cl)$, PM free base = 577.

N.M.R. (DMSO-$d_6$): $\delta$ 2.64 (2H, b); 3.2–3.8 (10H, m); 6.40–7.25 (6H, m); 8.20 (H, t); 8.62 (2H, s); 8.90 (2H, s); 9.78 (2H, s); 9.88 (H, s).

EXAMPLE 3

To an ice-cooled solution of N-deformyl Distamycin A.hydrochloride (0.132 g) in 2 ml of DMF and 78 mg of 2,4,5-trichlorophenyl-N-methyl-N-nitrosocarbamate [Prepared according to J. Med. Chem. 25, 178 (1982)], a solution of diisopropylethylamine (0.041 ml) in 2 ml of DMF was added dropwise. The resulting solution was stirred 40' at 0° C. The reaction mixture was concentrated under vacuum and the residue was purified by column chromatography to yield 62 mg of N-deformyl-N-[N'-methyl-N'-nitrosocarbamoyl]-Distamycin A. hydrochloride.

UV (EtOH 95%) $\lambda$max 239, 306–8; $\epsilon$=21,611; $\epsilon$=28,207.

IR$_{KBr}$: $\nu$ cm$^{-1}$ 3500–2800; 2500–2200; 1460; 970; 660.

NMR$_{DMSO-d_6}$: $\delta$ 2.63 (2H, m); 3.17 (3H, s); 3.48 (2H, m); 3.81 (3H, s); 3.84 (3H, s); 3.87 (3H, s); 6.90–7.27 (6H, m); 8.17 (1H, bt); 8.62 (2H, bt); 8.98 (2H, br); 9.86 (1H, bs); 9.93 (1H, bs); 10.66 (1H, bs).

By analogous procedure the following compound was obtained:

N-deformyl-N-[N'-(2-chloroethyl)-N'-nitrosocarbamoyl]-Distamycin A. hydrochloride, N.M.R. (DMSO-$d_6$): $\delta$ 2.61 (2H, t); 3.50 (2H, dt); 3.65 (2H, t); 3.81 (3H, s); 3.86 (3H, s); 3.89 (3H, s); 4.19 (2H, t); 6.90–7.25 (6H, m); 8.18 (1H, t); 8.56 (2H, s); 8.94 (2H, s); 9.88 (1H, s); 9.93 (1H, s); 10.93 (1H, s); U.V. (EtOH 95%): $\lambda$max 240 $\epsilon$=30,286; $\lambda$max 310 $\epsilon$=42,783.

EXAMPLE 4

To a solution of (2R,3R)-3-methyloxirane carboxylic acid (153 mg) in dry THF (4 ml) cooled to $-20°$ C., N-methylmorpholine (0.165 ml) was added, and then pivaloyl chloride (0.184 ml). The resulting suspension was stirred at $-20°$ C. for 20 minutes, then the whole was added to a cooled solution of N-deformyl Distamycin A (500 mg) in DMF (10 ml) and NaHCO$_3$ (80 mg). The mixture was stirred for 30 minutes at 0° C., and then for 4 hours at room temperature. Solvents were evaporated in vacuum to dryness, and the residue chromatographed in SiO$_2$ (solvent: CHCl$_3$ 80/CH$_3$OH 20) to yield 280 mg of N-deformyl-N-[3-methyl-(2R, 3R)oxirane-1-carbonyl]Distamycin A. hydrochloride. N.M.R.

(DMSO-d$_6$): δ1.26 (3H, d); 3.3 (1H, m); 3.60 (1H, d) [J4.7 H$_z$(cis)].

By analogous procedure the following compounds were obtained:

N-deformyl-N-(2-chloroethylcarbonyl)Distamycin A.hydrochloride, m.p. 160° C. (dec.), N.M.R. (DMSO-d$_6$): δ 2.67 (2H, bt); 2.75 (2H, t); 3.52 (2H, m); 3.81 (3H, s); 3.84 (6H, s); 3.87 (2H, t); 6.85–7.30 (6H, m); 8.22 (1H, bt); 8.74 (2H, br); 9.04 (2H, br); 9.90 (2H, ds); 10.08 (1H, bs); U.V. (EtOH 95%): λmax 241 ε=26,283; λmax 307 ε=33,420.

N-deformyl-N-(3-methyloxiranecarbonyl)Distamycin A.hydrochloride, N.M.R. (DMSO-d$_6$): δ1.26 (3H, d); 3.3 (1H, m); 3.60 (1H, d) [J4.7 H$_z$(cis)]; N-deformyl-N-(cyclopropylcarbonyl)Distamycin A.hydrochloride, N.M.R. (DMSO-d$_6$): δ0.75 (4H, m); 1.76 (1H, m); 2.65 (2H, t); 3.52 (2H, m); 3.83 (9H, s); 6.8–7.3 (6H, m); 8.21 (1H, bt); 8.69 (2H, bt); 9.00 (2H, br); 9.88 (2H, bs); 10.09 (1H, s); U.V. (EtOH 95%): λmax 241 ε=28,471; λmax 309 ε=33,125.

N-deformyl-N-[1-(aziridine)carbonyl]Distamycin A.hydrochloride, N.M.R. (DMSO-d$_6$): δ2.08 (4H, s); 2.65 (2H, t); 3.52 (2H, m); 3.70–3.90 (9H, m); 6.80–7.25 (6H, m); 8.24 (1H, t); 8.95 (4H, bs); 9.70 (1H, s); 9.90 (2H, s); U.V. (EtOH 95%): λmax 242 ε=27,757; λmax 308 ε=33,287;

N-deformyl-N-(bromomethylcarbonyl)Distamycin A.hydrochloride, N.M.R. (DMSO-d$_6$): δ2.63 (2H, bt); 3.51 (2H, dt); 3.81 (3H, s); 3.84 (6H, s); 4.20 (2H, s); 6.9–7.35 (6H, m); 8.12 (1H, t); 8.53 (2H, br); 8.94 (2H, br); 9.87 (1H, s); 9.90 (1H, s); 10.28 (1H, s);

N-deformyl-N-(oxiranecarbonyl)Distamycin A.hydrochloride, N.M.R. (DMSO-d$_6$): δ2.64 (2H, m); 2.89 (2H, m); 3.50 (2H, m); 3.55 (1H, dd); 3.81 (3H, s); 3.84 (6H, s); 6.9–7.3 (6H, m); 8.22 (1H, bt); 8.4–9.4 (4H, br); 9.9 (3H, br).

We claim:

1. A compound of formula (I)

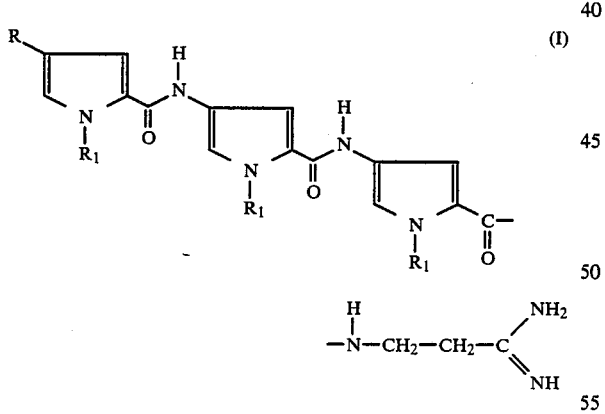

wherein

R is (a) —NHR$_3$, wherein R$_3$ is
  (a') —CON(NO)R$_4$, in which R$_4$ is C$_1$–C$_4$ alkyl either unsubstituted or substituted by halogen; or
  (b') —CO(CH$_2$)$_m$—R$_5$, in which R$_5$ is halogen, oxiranyl, methyloxiranyl, aziridinyl, a group

or a group

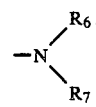

and m is zero or an integer of 1 to 4; or (b)

wherein either R$_6$ and R$_7$ are the same and are each oxiranemethyl, aziridinemethyl, or C$_2$–C$_4$ alkyl 2-substituted by halogen or by a group —OSO$_2$R$_8$, wherein R$_8$ is C$_1$–C$_4$ alkyl or phenyl, or one of R$_6$ and R$_7$ is hydrogen and the other is as defined above; and each group R$_1$ is, independently, hydrogen or C$_1$–C$_4$ alkyl, and the pharmaceutically acceptable salts thereof.

2. A compound of formula (I), according to claim 1, wherein
R is —NHR$_3$, wherein R$_3$ is
  (a') —CON(NO)R$_4$ wherein R$_4$ is C$_1$–C$_4$ alkyl substituted by halogen, or
  (b') —CO(CH$_2$)$_m$—R$_5$ wherein R$_5$ is halogen, oxiranyl, 1-aziridinyl, a group

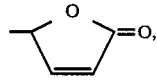

or a group

and m is zero, 1 or 2;
each group R$_1$ is, independently, C$_1$–C$_4$ alkyl, and the pharmaceutically acceptable salts thereof.

3. A compound of formula (I), according to claim 1, wherein R is

wherein R$_6$ and R$_7$ are the same and are each oxiranemethyl, 1-aziridinemethyl, or a C$_2$–C$_4$ alkyl group 2-substituted by halogen or by a group —OSO$_2$R$_8$ wherein R$_8$ is C$_1$–C$_4$ alkyl; each group R$_1$ is, independently, C$_1$–C$_4$ alkyl, and the pharmaceutically acceptable salts thereof.

4. A compound of formula (I) as defined in claim 1 selected from the group consisting of:
  N-deformyl-N-[N'-(2-chloroethyl)-N'-nitrosocarbamoyl]-Distamycin A;
  N-deformyl-N-[N'-methyl-N'-nitrosocarbamoyl]-Distamycin A;
  N-deformyl-N-(oxiranecarbonyl)Distamycin A;
  N-deformyl-N-(3-methyloxiranecarbonyl)Distamycin A;

N-deformyl-N-(2-chloroethylcarbonyl)Distamycin A;

N-deformyl-N-[1-(aziridine)carbonyl]Distamycin A;

N-deformyl-N-[N,N-bis(2-chloroethyl)]Distamycin A.

5. A hydrochloric acid salt of a compound of formula (I) as claimed in claim 4.

6. A pharmaceutical antiviral or antitumor composition containing a suitable carrier and/or diluent and, as an active principle, an effective amount of compound of formula (I) or pharmaceutically acceptable salt thereof.

* * * * *